(12) United States Patent
King et al.

(10) Patent No.: US 6,964,780 B1
(45) Date of Patent: Nov. 15, 2005

(54) CONTROLLED-RELEASE PHARMACEUTICAL FORMULATIONS

(75) Inventors: Elizabeth King, Sandwich (GB); Ross James Macrae, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/425,622

(22) Filed: Oct. 22, 1999

(30) Foreign Application Priority Data

| Oct. 23, 1998 | (GB) | 9823192 |
| Oct. 27, 1998 | (GB) | 9826392 |
| Nov. 16, 1998 | (GB) | 9825117 |

(51) Int. Cl.[7] ............ A61K 9/22; A61K 9/26; A61K 9/32; A61K 9/36
(52) U.S. Cl. ........ 424/473; 424/468; 424/469; 424/472; 424/474; 424/480; 424/482
(58) Field of Search ............ 424/468, 469, 424/470, 473, 457, 458, 462, 474, 480, 482, 424/484, 488, 490, 497, 475, 472

(56) References Cited

U.S. PATENT DOCUMENTS

| 3,952,741 | A |   | 4/1976  | Baker .............. 128/260 |
| 5,112,621 | A |   | 5/1992  | Stevens et al. ........ 424/497 |
| 5,464,633 | A |   | 11/1995 | Conte et al. .......... 424/480 |
| 5,474,784 | A |   | 12/1995 | Stevens et al. ........ 424/456 |
| 5,656,629 | A | * | 8/1997  | Bacon et al. ........ 514/234.5 |
| 5,874,418 | A | * | 2/1999  | Stella et al. .......... 514/58 |
| 6,046,177 | A | * | 4/2000  | Stella et al. .......... 514/58 |
| 6,077,841 | A | * | 6/2000  | Sui et al. .......... 514/234.2 |
| 6,277,884 | B1 | * | 8/2001  | de Tejada .......... 514/565 |
| 6,403,597 | B1 | * | 6/2002  | Wilson et al. .......... 514/256 |

FOREIGN PATENT DOCUMENTS

| EP | 0393572   | 10/1990 | ........ A61K 31/445 |
| EP | 0463756   | 1/1992  | ........ C07D 487/04 |
| EP | 0526004   | 2/1993  | ........ C07D 487/04 |
| WO | WO9428902 | 12/1994 | ........ A61K 31/505 |
| WO | WO9703675 | 2/1997  | ........ A61K 31/495 |
| WO | WO9718814 | 5/1997  | ........ A61K 31/505 |
| WO | WO9748382 | 12/1997 | ........ A61K 9/16 |
| WO | WO9830209 | 7/1998  | ........ A61K 9/54 |
| WO | WO9848781 | 11/1998 | ........ A61K 9/22 |

OTHER PUBLICATIONS

Drugs and the Pharmaceutical Sciences, edited by J. R. Robinson, published by Marcel Dekker Inc., pp. 3-6.
J. A. Beavo and D. H. Reifsnyder, Trends Pharmacol Sci 11:150, 1990, pp. 150-155.
Cyclic Nucleotide Phosphodiesterases: Structure, Regulation and Drug Action, edited by J. Beavo and M. D. Houslay, 1990, pp. 3-15.
Zrnei-formenlehre; Ein Lehrbuch der galenick fur Theorie and Praxis; Von Dr. Ursula Schoffling, Trier, 1998, 199-205.
Arznei-formenlehre; Ein Lehrbuch der galenick fur Theorie and Praxis; Von Dr. Ursula Schoffling, Trier, 1998, 199-205 (English Translation).

* cited by examiner

*Primary Examiner*—James M. Spear
(74) *Attorney, Agent, or Firm*—Gregg C. Benson; Martha G. Munchhof

(57) ABSTRACT

The invention provides controlled-release formulations for oral administration containing a cGMP PDE-5 inhibitor. The formulations are useful, inter alia, in the treatment or prevention of sexual dysfunction.

26 Claims, 1 Drawing Sheet

CONTROLLED-RELEASE PHARMACEUTICAL FORMULATIONS

This invention relates to controlled-release oral pharmaceutical formulations of cGMP PDE-5 inhibitors, and to methods of treatment involving them.

Controlled-release oral pharmaceutical formulations are known. Their purpose is to modify the rate of drug release, for example to produce a constant rate of release of a drug into the gastrointestinal tract of a patient, or to delay the release of a drug into the gastrointestinal tract of a patient (see 'Sustained and Controlled Release Drug Delivery Systems', pp 3–6, edited by J R Robinson, published by Marcel Dekker Inc).

Cyclic nucleotide phosphodiesterases (PDEs) are a family of enzymes that catalyse the degradation of cyclic nucleotides. Cyclic nucleotides, particularly cAMP (i.e. cyclic adenosine 3',5'-monophosphate), are important intracellular second messengers. PDEs are one cellular component that regulates the concentration of cyclic nucleotides. In recent years, at least seven PDE enzymes (such as PDE-1–PDE-7), as well as many subtypes of these enzymes, have been defined based on substrate affinity and cofactor requirements (J A Beavo and D H Reifsnyder, Trends Pharmacol Sci 11:150 [1990]; and J Beavo, in 'Cyclic Nucleotide Phosphodiesterases: Structure, Regulation and Drug Action', (Editors J Beavo and M D Housley). Wiley, Chichester, pp. 3–15 [1990]).

PDE-5 is a cGMP (i.e. cyclic guanosine 3',5'-monophosphate) specific PDE. It has been shown that PDE-5 is an important enzyme in regulating the physiological response to sexual stimulation, and that inhibitors of the enzyme are useful in the treatment of sexual dysfunction.

In males, sexual dysfunction may be defined as the inability to obtain or sustain a penile erection adequate for satisfactory sexual intercourse. In females, sexual dysfunction may be defined as deficient physiological response to sexual stimulation and/or a deficient subjective feeling of arousal.

A cGMP PDE-5 inhibitor of particular interest is sildenafil {5-[2-ethoxy-5-(4-methyl-1-piperazinylsulphonyl)phenyl]-1,6-dihydro-1-methyl-3-propylpyrazolo[4,3-d]pyrimidin-7-one}, which has the following structure:

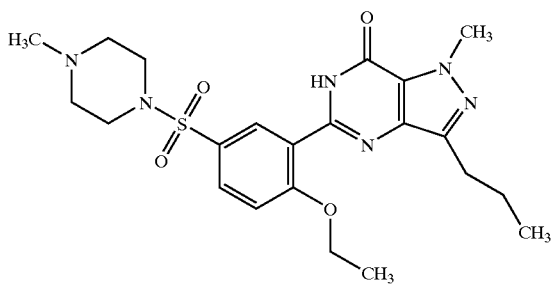

The compound was first disclosed in European Patent Application 463756, and its use in the treatment of sexual dysfunction was disclosed in International Patent Application WO 94/28902. A formulation of the citrate salt (VIAGRA™) was made available for the treatment of male erectile dysfunction in a number of countries including the USA in 1998. VIAGRA™ is an immediate release tablet that is administered about 1 hour before an effect is required, and the half-life of the drug in human plasma is about 4 hours after administration.

The main interest in the art so far has been to provide a fast-acting treatment of sexual dysfunction, which can provide an effect as soon as possible after administration. For example, International Patent Application WO 98/30209 discloses a rapidly releasing formulation of sildenafil citrate.

International Patent Application WO 97/18814 discloses controlled-release pharmaceutical formulations for oral administration consisting essentially of an active ingredient, low molecular weight polyethylene oxide, hydroxypropylmethyl cellulose, tabletting excipients, and optionally one or more enteric polymers. It is suggested therein that sildenafil could be delivered using the disclosed formulations. However, the advantages given below for controlled-release formulations of cGMP PDE-5 inhibitors were not mentioned.

International Patent Application WO 98/48781 (published on 5 Nov. 1998, after the priority date of the present application) discloses compositions providing "relatively slow release" of compounds including apomorphine (which is not a cGMP PDE-5 inhibitor). The formulations are indicated in the treatment of sexual dysfunction.

According to the present invention, there is provided a controlled-release formulation for oral administration containing a cGMP PDE-5 inhibitor; provided that the formulation does not consist essentially of sildenafil, low molecular weight polyethylene oxide, hydroxypropylmethyl cellulose, tabletting excipients, and optionally one or more enteric polymers.

Usually, formulations according to the invention will be tablets or capsules that are swallowed. However, the invention also includes buccal formulations (which may be tablets, ointments, gels or patches).

Controlled-release formulations may be divided into sustained-release and pulsatile-release formulations (also known as delayed-release formulations). In general, such formulations are known to those skilled in the art or are available using conventional methods.

Sustained-release dosage forms release their active ingredient into the gastro-intestinal tract of a patient over a sustained period of time following administration of the dosage form to the patient. Particular dosage forms include:

(a) those in which the active ingredient is embedded in a matrix from which it is released by diffusion or erosion (see Example 1 below);
(b) those in which the active ingredient is present in a core which is coated with a release rate-controlling membrane (see Example 3 below);
(c) those in which the active ingredient is present in a core provided with an outer coating impermeable to the active ingredient, the outer coating having an aperture (which may be drilled) for release of the active ingredient;
(d) those in which the active ingredient is released through a semi-permeable membrane, allowing the drug to diffuse across the membrane or through liquid filled pores within the membrane; and
(e) those in which the active ingredient is present as an ion exchange complex.

The dosage forms mentioned in (a), (b) and (c) above are of particular interest.

When several cores are present, for example coated cores in the dosage forms mentioned in (b) and (c), such formulations are sometimes referred to as "multiparticulates".

It will be apparent to those skilled in the art that some of the above means of achieving sustained-release may be combined, for example a matrix containing the active compound may be formed into a multiparticulate and/or coated with an impermeable coating provided with an aperture.

Pulsatile-release formulations release the active compound after a sustained period of time following administration of the dosage form to the patient. The release may then be in the form of immediate- or sustained-release. This delay may be achieved by releasing the drug at particular points in the gastro-intestinal tract or by releasing drug after a pre-determined time. Pulsed-release formulations may be in the form of tablets or multiparticulates or a combination of both. Particular dosage forms include:

1. osmotic potential triggered release (see U.S. Pat. No. 3,952,741);
2. compression coated two layer tablets (see U.S. Pat. No. 5,464,633);
3. capsules containing an erodible plug (see U.S. Pat. No. 5,474,784);
4. sigmoidal releasing pellets (referred to in U.S. Pat. No. 5,112,621); and
5. formulations coated with or containing pH-dependent polymers including shellac, phthalate derivatives, polyacrylic acid derivatives and crotonic acid copolymers.

Dual release formulations can combine the active ingredient in immediate release form with additional active ingredient in controlled-release form. For example, a bilayer tablet can be formed with one layer containing immediate release active ingredient and the other layer containing the active ingredient embedded in a matrix from which it is released by diffusion or erosion. Alternatively, one or more immediate release beads can be combined with one or more beads which are coated with a release rate-controlling membrane in a capsule to give a dual release formulation. Sustained release formulations in which the active ingredient is present in a core provided with an outer coating impermeable to the active ingredient, the outer coating having an aperture (which may be drilled) for release of the active ingredient, can be coated with drug in immediate release form to give a dual release formulation. Dual release formulations can also combine drug in immediate release form with additional drug in pulsed release form. For example, a capsule containing an erodible plug could liberate drug initially and after a predetermined period of time further drug in immediate- or sustained-release form.

Thus, according to the invention, there is further provided a dual release formulation for oral administration having a first portion comprising a controlled-release formulation as defined above, but without proviso, and a second portion comprising a cGMP PDE-5 inhibitor in immediate release form. The invention also provides products containing a controlled-release formulation as defined above, but without proviso, and a cGMP PDE-5 inhibitor in immediate release form, as a combined preparation for simultaneous, separate or sequential use in the treatment or prevention of sexual dysfunction.

Preferably, formulations according to the present invention are sustained-release formulations. For example, it is preferred that up to 75% by weight of the active ingredient is released from the formulation into the gastrointestinal tract (or in a model of the GI tract) after a period of time in the range 1–24 hours following administration, for example 6–18 hours. A suitable model of the GI tract is described in Example 2 below.

Dual release formulations as defined above are also of particular interest. It is preferred that the first portion of such formulations is a sustained-release formulation.

An advantage of controlled-release, particularly sustained-release formulations according to the present invention is that a patient receiving them would have improved sexual function for a sustained period of time following administration (such as 6–24 hours, for example 12–18 hours), and so be ready for sexual activity at almost any time. This would allow a more spontaneous sex-life to be pursued.

In addition, it is thought that in male patients at risk of developing sexual dysfunction (for example diabetic patients or patients having undergone nerve sparing radical prostatectomy), the prevalence of nocturnal erections is diminished. Nocturnal erections may play an important role in preserving normal erectile function by providing regular tissue oxygenation thus preventing tissue fibrosis and erectile degeneration. Thus, a cGMP PDE-5 inhibitor delivered to a patient during sleep will increase the ability of at-risk individuals to have nocturnal erections, increase tissue oxygenation, prevent penile fibrosis and thus preserve erectile function or slows its decline. Controlled-release formulations may be of particular use in this instance, providing cGMP PDE-5 inhibition throughout the sleeping period.

A further advantage of formulations according to the present invention is that side effects may be reduced. For example, although sildenafil offers a safe, effective and generally very well tolerated oral treatment for male erectile dysfunction, dose-related reversible side effects such as headache or visual disturbance at high dosage may limit its use in a minority of patients. Such effects are mediated by systemic exposure to sildenafil following oral administration: thus a formulation with a sustained release profile, which avoids initial high plasma concentrations, could be of great value to these patients.

Preferably, the cGMP PDE-5 inhibitor is sildenafil, or a pharmaceutically acceptable salt thereof (such as the citrate salt).

Other cGMP PDE-5 inhibitors (previously mentioned in WO 94/28902) that may be mentioned include:

5-(2-ethoxy-5-morpholinoacetylphenyl)-1-methyl-3-n-propyl-1,6-dihydro-7H -pyrazolo[4,3-d]pyrimidin-7-one.

5-(5-morpholinoacetyl-2-n-propoxyphenyl)-1-methyl-3-n-propyl-1,6-dihydro-7H -pyrazolo[4,3-d]pyrimidin-7-one;

5-[2-allyloxy-5-(4-methyl-1-piperazinylsulphonyl)phenyl]-1-methyl-3-n-propyl-1,6-dihydro-7H-pyrazolo[4,3-d]pyrimidin-7-one;

5-{2-ethoxy-5-[4-(2-propyl)-1-piperazinylsulphonyl]phenyl}-1-methyl-3-n-propyl-1,6-dihydro-7H-pyrazolo[4,3-d]pyrimidin-7-one;

5-{2-ethoxy-5-[4-(2-hydroxyethyl)-1-piperazinylsulphonyl]phenyl}-1-methyl-3-n-propy- 1,6-dihydro-7H-pyrazolo [4,3-d]pyrimidin-7-one;

5-{5-[4-(2-hydroxyethyl)-1-piperazinylsulphonyl]-2-n-propoxyphenyl}-1-methyl-3-n -propyl-1,6-dihydro-7H-pyrazolo[4,3-d]pyrimidin-7-one;

5-[2-ethoxy-5-(4-methyl-1-piperazinylcarbonyl)phenyl]-1-methyl-3-n-propyl-1,6-dihydro -7H-pyrazolo[4,3-d]pyrimidin-7-one; and 5-[2-ethoxy-5-(1-methyl-2-imidazolyl)phenyl]-1-methyl-3-n-propyl-1,6-dihydro-7H -pyrazolo[4,3-d]pyrimidin-7-one.

The following cGMP PDE-5 inhibitors (previously mentioned in WO 97/03675 to Laboratoire Glaxo Wellcome SA) may also be mentioned:

(6R,12aR)-2,3,6,7,12,12a-hexahydro-2-methyl-6-(3,4-methylenedioxyphenyl) -pyrazino[2',1':6,1]pyrido[3,4-b]indole-1,4-dione; and (3S,6R,12aR)-2,3,6,7,12,12a-hexahydro-2,3-dimethyl-6-(3,4-methylenedioxyphenyl) -pyrazino[2',1':6,1]pyrido[3,4-b]indole- 1,4-dione.

When the formulation includes a matrix in which the active ingredient is embedded (such as a matrix tablet), it preferably contains hydroxypropylmethyl cellulose. Preferably, the hydroxypropylmethyl cellulose has a number average molecular weight in the range 80,000–250,000. Preferably, the hydroxypropylmethyl cellulose has a degree of methyl substitution in the range 19–30%. Preferably, the hydroxypropylmethyl cellulose has a degree of hydroxy substitution in the range 7–12%. A number of hydroxypropylmethyl cellulose polymers are available commercially under the brand name Methocel™, and some of those suitable for use in formulations according to the invention are given in the table below:

| Methocel ™ grade | Number average MW | Degree of methyl substitution | Degree of hydroxy substitution | Nominal viscosity of a 2% aqueous solution | USP designation |
|---|---|---|---|---|---|
| K4M | 89000 | 19–24% | 7–12% | 4000 cps | 2208 |
| K15M | 125000 | " | " | 15000 cps | " |
| K100M | 215000 | " | " | 1000000 cps | " |
| E4M | 93000 | 28–30% | 7–12% | 4000 cps | 2910 |
| E10M | 113000 | " | " | 10000 cps | " |
| F4M | 90000 | 27–30% | 4–7.5% | 4000 cps | 2906 |

Methocel ™ K4M has characteristics of particular interest.

It will be apparent to those skilled in the art that the hydroxypropylmethyl cellulose may consist of molecules of different chain lengths, but that the average chain length gives a molecular weight in the range stated.

Matrix formulations according to the present invention may contain a buffering agent. This is particularly useful when the formulation contains sildenafil citrate. A buffering agent of particular interest is aspartic acid. When it forms part of a matrix tablet, aspartic acid acts as a buffering agent to maintain a low pH at the surface of the tablet. Because sildenafil citrate has a low solubility at pH values greater than 6, the acid keeps the drug relatively soluble during the transit of the tablet through the GI tract. When present, aspartic acid will typically make up 15–30% by weight of the formulation.

The formulations of the present invention may include tabletting excipients, for example colloidal anhydrous silica, polyvinylpyrrolidone, lactose and magnesium stearate. Lactose is of particular interest, and when present it will typically make up 10–40% by weight of the formulation.

Formulations according to the invention may be provided additionally with a cosmetic coating: for example a coating comprising a pigment, a plasticizer and a polymer such as OPADRY™ (manufactured by Colorcon), or a sugar coating. Such coatings do not substantially affect the performance of the formulation, but enhance its presentation. Such coatings may be applied by spraying tablet cores with a solution of the components, using conventional techniques.

Preferably, in matrix formulations according to the present invention, the hydroxypropylmethyl cellulose makes up 10–50% by weight of the formulation.

When the formulation has a core comprising the active ingredient which is coated with a release rate-controlling membrane, it is preferred that several such coated cores are present (i.e. the formulation is multiparticulate). For example, 100 or more coated cores may be filled into a capsule. Preferably, the core also includes a buffering agent (such as succinic acid). The release rate-controlling membrane may comprise an ammonio methacrylate copolymer and a plasticizer.

Preferably, in formulations according to the present invention, the cGMP PDE-5 inhibitor makes up 5–50% by weight of the formulation.

Preferably, in formulations according to the present invention, the rate at which the cGMP PDE-5 inhibitor is released therefrom is substantially independent of the pH of the surroundings.

The present invention also provides processes for the production of the sustained release pharmaceutical formulations set out in (a), (b) and (c) above, which include the steps of:

(a) mixing the cGMP PDE-5 inhibitor with a matrix material, and pressing into tablets;

(b) forming a core comprising the cGMP PDE-5 inhibitor and then coating the core with a release rate-controlling membrane; or (c) forming a core containing the cGMP PDE-5 inhibitor and then coating the core with a coating impermeable to the cGMP PDE-5 inhibitor:

respectively.

The invention further provides the use of a cGMP PDE-5 inhibitor in the manufacture of a formulation for the treatment or prevention of sexual dysfunction; characterized in that, following administration, the formulation releases the inhibitor over or after a sustained period of time. Consequently, following administration, the mammal's sexual function will be substantially improved for or after a sustained period of time.

Usually, the mammal will be a human, but administration to other mammals, such as horses, is contemplated.

A "sustained period of time" in relation to the improvement in sexual function is a period of time such as $6 \geq 24$ hours, for example $12 \geq 18$ hours.

It will be appreciated by those skilled in the art that the formulations of the present application may also be administered to patients suffering from or at risk of suffering from disorders other than sexual dysfunction, but in which cGMP PDE-5 inhibitors may be useful therapeutically.

The invention further provides a method of treating or preventing sexual dysfunction, which comprises administering a controlled-release formulation of a cGMP PDE-5 inhibitor, as defined above, but without proviso, to a mammal in need of such treatment or prevention. Consequently, the mammal's sexual function is substantially improved for or after a sustained period of time.

The invention further provides a method of improving sexual function in a mammal (not suffering from sexual dysfunction), which comprises administering a controlled-release formulation of a cGMP PDE-5 inhibitor, as defined above, but without proviso, to the mammal. Consequently, the mammal's sexual function is substantially improved for or after a sustained period of time.

The invention further provides a method of increasing the probability of a nocturnal erection in a male mammal, which comprises administering a controlled-release formulation, as defined above, but without proviso, to the male mammal.

Formulations according to the invention will usually be administered once a day, or possibly twice a day. The total daily dosage of a cGMP PDE-5 inhibitor (such as sildenafil citrate) is usually in the range 25–400 mg, preferably 50–200 mg. Thus, a once daily formulation according to the invention will usually contain 25–400 mg of drug substance (such as sildenafil citrate), preferably 50–200 mg.

BRIEF DESCRIPTION OF THE DRAWING

The invention is illustrated by the following examples with reference to the accompanying drawing, in which.

EXAMPLE 1

Figure 1:
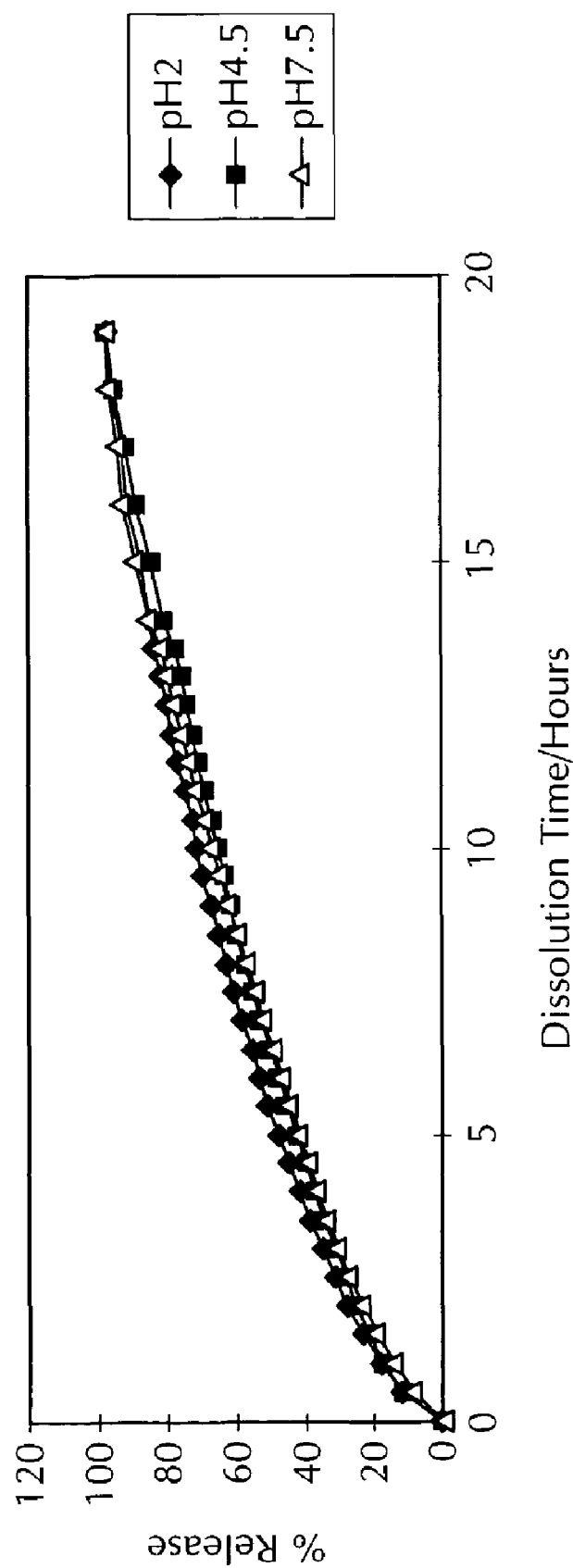
FIG. 1 shows the percentage of drug compound released v time from a formulation prepared according to Example 1 under three different pH conditions.

Sustained Release Matrix Formulation of Sildenafil Citrate

| Component | Weight per 450 mg matrix tablet (mg) |
|---|---|
| Sildenafil citrate | 144.72[a] |
| L-Aspartic acid | 100 |
| Hydroxypropylmethyl cellulose[b] | 67.5 (15%) |
| Lactose[c] | 133.28 |
| Magnesium Stearate | 4.5 |

[a]Drug equivalent to 100 mg active substance based on actual activity of 69.1%.
[b]Methocel ™ grade K4M
[c]Lactose fastflo Method
1. Blend components, less magnesium stearate, for 10 minutes in a turbula
2. Screen through a 500 μm sieve
3. Add 26% water (by weight) with blending
4. Screen through a 1.7 mm sieve
5. Dry resulting granules in a vacuum oven at 40° C. 2070 kPa (300 psi) until the moisture level is returned to original value
6. Screen through a 1.0 mm sieve
7. Add magnesium stearate and blend for 5 minutes
8. Press into tablets using 11 mm normal concave tablet tooling

EXAMPLE 2

Dissolution Studies

Formulations prepared in Example 1 were dissolved using Apparatus 1 (baskets) described in United States Pharmacopeia 23 (1995), page 1791, in an aqueous buffer of pH 2 (composition 0.01M HCl and 0.12M NaCl), an aqueous buffer of pH 4.5 (composition 0.06M KCl, 0.03M NaCl and 0.006M KH$_2$PO$_4$) and in an aqueous buffer of pH 7.5 (composition 0.06M KCl, 0.03M NaCl. 0.006M KH$_2$PO$_4$ and 0.005M NaOH). The dissolution fluid volume was 1 l in the case of pH 2 and pH 4.5, but 5 l in the case of pH 7.5 (also replaced periodically), the temperature was 37° C., the rotation speed of the baskets was 100 rpm, and the drug compound released was detected by UV spectroscopy. The percentage of drug compound released v time is shown in FIG. 1.

It can be seen that the release profiles at the three pH values are almost identical, indicating that the formulation is likely to give a steady, sustained rate of release of drug over a sustained period of time when administered orally to a patient.

EXAMPLE 3

Sustained-Release Coated Multiparticulate Core Formulation of Sildenafil Citrate The formulation is prepared by applying a polymer coat onto core beads. These are then encapsulated.

Step 1 : Preparation of Multiparticulate Cores

| Ingredient | Composition mg/50 mg dose |
|---|---|
| Sildenafil citrate | 71.9[a] |
| Microcrystalline cellulose[b] | 73.5 |
| Lactose[c] | 73.5 |
| Succinic acid | 93.8 |
| (Water)[d] | (109.5) |
| Total: | 312.7 |

[a]Drug equivalent to 50 mg active substance based on theoretical activity of 69.5%.
[b]Avicel ™ PH101.
[c]Lactose fastflo.
[d]Removed during drying. Quantity varied with batch size.

All of the dry ingredients are blended together in a Turbula blender for 20 minutes. The mixture is then screened using a 500 μm (30 mesh) screen followed by reblending for a further 20 minutes. Wet granulation is performed in a planetary mixer by carefully adding water to the mixture while continuously blending at a low speed. Cores are produced from the wet granules by a conventional extrusion and spheronisation process. The formed cores are then dried in a standard fluidised-bed drier.

Step 2: Coating of Multiparticulate Cores

| Ingredient | Composition mg/50 mg dose |
|---|---|
| Cores from step 1 | 312.7 |
| Ammonio methcrylate copolymer type B[a] | 31.27 |
| Ammonio methacrylate copolymer type A[b] | 7.82 |
| Triethyl citrate | 7.82 |
| Talc | 19.55 |
| (Water)[d] | (332.3) |
| Total: | 379.16 |

[a]Eudragit ™ RS 30 D.
[b]Eudragit ™ RL 30 D.

To prepare the coating, all of the ingredients except the active cores are mixed together to form a uniform dispersion. The mixture is applied to the cores by a conventional fluidised-bed spray coating technique to give the final coated cores. Typically, these coated cores may then be cured at 40° C. for 18 hours. They are then filled into gelatin capsule shells using conventional encapsulating equipment.

What is claimed is:

1. A sustained-release formulation for oral administration containing a cGMP PDE-5 inhibitor, which comprises a core containing the cGMP PDE-5 inhibitor and an outer coating impermeable to the cGMP PDE-5 inhibitor, the outer coating having an aperture for release of the cGMP PDE-5 inhibitor, provided that the formulation does not consist essentially of sildenafil, low molecular weight polyethylene oxide, hydroxypropylmethyl cellulose, tabletting excipients, and optionally one or more enteric polymers.

2. A sustained-release formulation for oral administration containing hydroxypropylmethyl cellulose and containing a cGMP PDE-5 inhibitor embedded in a matrix from which it is released by diffusion or erosion; provided that the formulation does not consist essentially of sildenafil, low molecular weight polyethylene oxide, hydroxypropylmethyl cellulose, tabletting excipients, and optionally one or more enteric polymers.

3. A sustained-release formulation for oral administration containing a buffering agent and a cGMP PDE-5 inhibitor embedded in a matrix from which it is released by diffusion or erosion, provided that the formulation does not consist essentially of sildenafil, low molecular weight polyethylene oxide, hydroxypropylmethyl cellulose, tabletting excipients, and optionally one or more enteric polymers.

4. A formulation as claimed in claim 2, wherein the hydroxypropylmethyl cellulose has a number average molecular weight in the range 80,000–250,000.

5. A formulation as claimed in claim 2, wherein the hydroxypropylmethyl cellulose has a degree of methyl substitution in the range 19–30%.

6. A formulation as claimed in claim 2, wherein the hydroxypropylmethyl cellulose has a degree of hydroxy substitution in the range 7–12%.

7. A formulation as claimed in claim 2, wherein the hydroxypropylmethyl cellulose makes up 10–50% by weight of the formulation.

8. A sustained-release formulation for oral administration containing a cGMP PDE-5 inhibitor, wherein the cGMP PDE-5 inhibitor is present in a core which is coated with a release rate-controlling membrane, provided that the formulation does not consist essentially of sildenafil, low molecular weight polyethylene oxide, hydroxypropylmethyl cellulose, tabletting excipients, and optionally one or more enteric polymers, wherein the release rate-controlling membrane comprises an ammonio methacrylate copolymer and a plasticizer.

9. A process for the production of a sustained-release formulation comprising a cGMP PDE-5 inhibitor embedded in a matrix from which it is released by diffusion or erosion, which comprises the steps of:
   (a) mixing the cGMP PDE-5 inhibitor with a matrix material, and pressing into tablets;
   (b) forming a core comprising the cGMP PDE-5 inhibitor and then coating the core with a release rate-controlling membrane; or
   (c) forming a core containing the cGMP PDE-5 inhibitor and then coating the core with a coating impermeable to the cGMP PDE-5 inhibitor;
respectively.

10. A method of treating sexual dysfunction, which comprises administering a sustained-release formulation, as defined in claim 1, to a mammal in need of such treatment.

11. The method of claim 10, characterized in that, following administration, the mammal's sexual function is substantially improved for or after a sustained period of time.

12. A method of improving sexual function in a mammal, which comprises administering a sustained-release formulation, as defined in claim 1, to the mammal.

13. The method of claim 12, characterized in that, following administration, the mammal's sexual function is substantially improved for or after a sustained period of time.

14. A method of increasing the probability of a nocturnal erection in a male mammal, which comprises administering a sustained-release formulation, as defined in claim 1, to the male mammal.

15. A dual release formulation for oral administration having a first portion comprising a controlled-release formulation comprising a cGMP PDE-5 inhibitor and a second portion comprising a cGMP PDE-5 inhibitor in immediate release form.

16. A product containing a controlled-release formulation comprising a cGMP PDE-5 inhibitor and a cGMP PDE-5 inhibitor in immediate release form, as a combined preparation for simultaneous, separate or sequential use in the treatment of sexual dysfunction.

17. A formulation as claimed in claim 1, wherein the cGMP PDE-5 inhibitor is sildenafil or a pharmaceutically acceptable salt thereof.

18. A formulation as claimed in claim 1, wherein the cGMP PDE-5 inhibitor is sildenafil citrate.

19. A formulation as claimed in claim 15, wherein the cGMP PDE-5 inhibitor is sildenafil or a pharmaceutically acceptable salt thereof.

20. A formulation as claimed in claim 15, wherein the cGMP PDE-5 inhibitor is sildenafil citrate.

21. A product as claimed in claim 16, wherein the controlled release formulation comprises sildenafil or a pharmaceutically acceptable salt thereof and wherein the immediate release formulation comprises sildenafil or a pharmaceutically acceptable salt thereof.

22. A product as claimed in claim 16, wherein the controlled release formulation comprises sildenafil citrate and wherein the immediate release formulation comprises sildenafil citrate.

23. A dual release formulation for oral administration as claimed in claim 15, having a first portion comprising a sustained release formulation comprising sildenafil or a pharmaceutically acceptable salt thereof and a second portion comprising sildenafil or a pharmaceutically acceptable salt thereof in immediate release form.

24. A dual release formulation for oral administration as claimed in claim 15, having a first portion comprising a sustained release formulation comprising sildenafil citrate and a second portion comprising sildenafil citrate in immediate release form.

25. A dual-release formulation for oral administration as claimed in claim 15, having a first portion comprising a controlled release formulation comprising sildenafil or a pharmaceutically acceptable salt thereof and a second portion comprising sildenafil or a pharmaceutically acceptable salt thereof in immediate release form, wherein a multiplicity of coated cores is present in the first portion.

26. A dual-release formulation for oral administration as claimed in claim 15, having a first portion comprising a controlled release formulation comprising sildenafil citrate and a second portion comprising sildenafil citrate in immediate release form, wherein a multiplicity of coated cores is present in the first portion.

* * * * *